United States Patent
Muntermann (12)

(10) Patent No.: US 7,524,276 B2
(45) Date of Patent: Apr. 28, 2009

(54) APPARATUS FOR TREATMENT WITH MAGNETIC FIELDS

(75) Inventor: Axel Muntermann, Wetzlar (DE)

(73) Assignee: Axel Muntermann, Wetzlar-Nauborn (DE)

( * ) Notice: Subject to any disclaimer, the term of this patent is extended or adjusted under 35 U.S.C. 154(b) by 0 days.

(21) Appl. No.: 10/597,740

(22) PCT Filed: Feb. 4, 2005

(86) PCT No.: PCT/EP2005/001161

§ 371 (c)(1), (2), (4) Date: Apr. 10, 2007

(87) PCT Pub. No.: WO2005/075019

PCT Pub. Date: Aug. 18, 2005

(65) Prior Publication Data

US 2008/0139871 A1    Jun. 12, 2008

(30) Foreign Application Priority Data

Feb. 6, 2004   (DE) .................. 10 2004 006 192

(51) Int. Cl.
*A61N 2/02* (2006.01)
(52) U.S. Cl. ........................................ 600/13
(58) Field of Classification Search ............... 600/9–15
See application file for complete search history.

(56) References Cited

U.S. PATENT DOCUMENTS

| 5,143,588 A | 9/1992 | Liboff et al. |
| 5,669,868 A | 9/1997 | Markoll |
| 6,447,440 B1 * | 9/2002 | Markoll ................ 600/13 |
| 6,461,289 B1 | 10/2002 | Muntermann |
| 6,558,311 B1 | 5/2003 | Muntermann |

FOREIGN PATENT DOCUMENTS

GB           429044           5/1935

OTHER PUBLICATIONS

International Preliminary Examination Report.

* cited by examiner

*Primary Examiner*—John P Lacyk
(74) *Attorney, Agent, or Firm*—DeMont & Breyer LLC

(57) ABSTRACT

The invention relates to an apparatus for therapeutic treatment of a patient with magnetic fields, in particular with nuclear magnetic resonances. One object is to provide an apparatus for treatment of a patient with magnetic fields, which in particular allows localized treatment, for example in the head area of the patient, which treatment places as little load as possible on the patient and can be used in a space-saving manner. A further aim is for the apparatus to have the capability to be flexibly matched to the anatomy of the patient and/or of the debilitation. The apparatus has a rest and at least one first cantilever arm (4B), which projects out of the plane defined by the rest (1C), with a device (30B) being arranged on the first cantilever arm (4B) in order to produce the first magnetic treatment field. The apparatus is particularly preferably in the form of a treatment stool or seat.

27 Claims, 9 Drawing Sheets

APPARATUS FOR TREATMENT WITH MAGNETIC FIELDS

FIELD OF THE INVENTION

The invention relates to an apparatus for therapeutic treatment of a patient using magnetic fields in general, and to an apparatus for treatment with nuclear magnetic resonances in particular.

BACKGROUND OF THE INVENTION

Non-invasive treatment processes are taking over more and more new fields of application in medicine. With reference to the invention proposed here, apparatuses and methods for therapeutic treatment by means of external magnetic fields should be mentioned in particular. Although, in the past, the precise method of operation of such therapies has not been understood in detail, their therapeutic successes have been scientifically proven and are generally recognized. Investigations relating to the results of known magnetic field therapies can be found, for example, in "Orthopädische Praxis" [Orthopedic Practice] 8/2000, Year 36, pages 510 to 515 and in Fritz Lechner, "Elektrostimulation und Magnetfeldtherapie. Anwendung, Ergebnisse and Qualitätssicherung" [Electrical stimulation and magnetic field therapy. Application, results and quality assurance] 1989.

In particular, it has been found during investigations such as these that magnetic field therapies for the patients in some cases produce considerable improvements in the symptoms without any significant verifiable negative side effects. A further major advantage of magnetic field therapies is that they may possibly make it possible to completely avoid an operation, which is associated with considerable pain, risks and costs for the patient.

For example, DE 40 26 173 discloses an apparatus which produces pulsed and modulated magnetic fields in order to treat patients. In this case, body tissue is subjected to a magnetic field which is produced by superimposition of a constant magnetic field and an alternating magnetic field.

The pulsating fields used there require a large amount of energy and are inert, however, since the coil inductance slows down the field change.

The therapeutic effect of this magnetic field therapy comprises inter alia the amelioration of osteoporosis and the consequences of a stroke. In this case, it appears to be probable that the magnetic fields produced promote transport and/or metabolic processes, which lead to a positive therapeutic effect. Until now, it has been assumed that the positive therapeutic effect is caused by an energy exchange between fields and components of cells (protons, ions, etc.). In this case, the energy transfer was explained by the excitation and the absorption of ion cyclotron resonances (ICR) in a biological body, and corresponding ICR conditions were therefore looked for. The known apparatuses are consistently based on the production of ICR conditions.

However, this cause explanation and thus the correspondingly designed apparatuses as well in some circumstances appear to be questionable, since cyclotron resonances in general occur only on free particles, for example in a vacuum or in the case of electrons in the conduction band of a semiconductor. Furthermore, it is also possible to show by simple calculation that a cyclotron movement would take place on a circular path whose radius is in its own right greater than the average diameter of the cross section of a human body. This means that an explanation relating to cyclotron resonance may be questionable for the energy transfer, in particular for solid tissue.

It is also possible that the effect may be based on piezo-electric processes in the body. This explanation approach assumes that an electrical field exists around every body joint and that, in the healthy state, every movement causes a piezo-voltage, since the cartilage has piezoelectric characteristics. In the debilitated state, these piezo-voltages could be simulated by induced voltages. In this context, see also Christian Thuile, "Das große Buch der Magnetfeldtherapie" [The textbook of magnetic field therapy], Linz 1997.

A further apparatus for treatment of a biological body with magnetic fields, which produces magnetic resonances within the body to be treated is known from Laid-Open Specification WO 99/66986. The apparatus described there is, however, essentially aimed at carrying out deliberately reproducible treatment with magnetic fields in all biological materials, irrespective of whether ionic parts are present. With the cited apparatus, the positive therapeutic effects are achieved by the production of magnetic resonances and magnetic resonance sequences. However, in this case, nuclear magnetic resonance is also used in particular for energy transfer.

Nuclear magnetic resonance methods (so-called NMR methods) have already been known for a long time from other fields of technology. They are used in particular for medical diagnosis and in general for high-precision magnetic-field measurement. With regard to the latter application, the "Virginia Scientific FW101 Flowing Water NMR Teslameter" may be cited by way of example. A description of this appliance can be found at: www.gmw.com/magnetic_measurements/VSI/FW101.html It should also be noted that the known apparatuses for therapeutic medicine generally have large coil systems which are used to generate and modify the magnetic fields. These coil systems have a high inductance, however, which leads to long switching time constants and to high energy consumption. Long switching times disadvantageously lead, however, to low efficiency in terms of dynamic processes in the body.

Furthermore, the coil systems are typically designed in such a manner that they have openings into which body parts for example arms or legs, can be introduced. In consequence, the known apparatuses are relatively inelegant and have disadvantages in terms of their storage and transport capabilities. Apart from this, in some cases, they are uncomfortable for the patient. Furthermore, the power consumption of most known apparatuses is very high, since strong magnetic fields are produced by means of the coil systems.

Furthermore, orthogonal fields are produced by these known apparatuses with orthogonal coils, that is to say a horizontal cylindrical coil produces a horizontal magnetic field, and a vertical saddle coil produces the vertical field. However, this means that the apparatus may be more than proportionally large, and can be installed only in large medical centers.

Furthermore, there remain a series of open questions relating to the physical/physiological operation of the apparatuses and to the processes which they initiate in the body. Without detailed knowledge of the method of operation, however, it has been difficult in the past to determine an optimized design and the optimum parameters for its operation.

Recently, apparatuses for therapeutic nuclear magnetic resonance processes have also been used in this field. One such apparatus is known, for example, from WO 02/096514, whose entire contents are hereby included by reference, in particular with respect to the physical principles and medical active mechanisms relating to the subject matter of this disclosure.

Particularly with the last-mentioned apparatus, it has already been possible to overcome some of the disadvantages referred to above, and to achieve considerable treatment success. Nevertheless, it has been found that the apparatus can be improved further, for example in terms of its size.

Furthermore, the apparatus is not equally well suited to the treatment of all debilitations.

In addition, the apparatus can be even better matched to the anatomic characteristics.

GENERAL DESCRIPTION OF THE INVENTION

The object of the invention is thus to provide an improved apparatus for treatment of a patient with magnetic fields, which in particular allows localized treatment, for example in the head area of the patient, and places as little load as possible on the patient.

A further object of the invention is to provide an apparatus such as this which can be used in a space-saving manner.

Another object of the invention is to provide an apparatus such as this which can be flexibly matched to the anatomy of the patient and/or to the debilitation, and which gives good treatment results.

A further object of the invention is to provide an apparatus such as this which can be manufactured and operated at low cost and is promising and inspires confidence for the patient.

The object of the invention is achieved in a surprisingly simple manner just by the subject matter of the independent claims. Advantageous developments of the invention are defined in the dependent claims.

According to the invention, an apparatus is proposed for therapeutic treatment of a patient, in particular of a living person or animal, using magnetic fields, which apparatus has at least one first device for production of a first magnetic treatment field. The apparatus defines one or more treatment areas in which a body region of the patient to be treated is positioned, once the patient is in place on the apparatus. The treatment is then carried out by means of the magnetic fields, which are injected into the treatment area or areas.

The apparatus also has a rest for the patient to rest on, in particular for the trunk or back of the patient, and has at least one first arm or cantilever arm, which projects at the side from the plane defined by the rest, or from the rest plane, that is to say it runs along the side of the patient transversely with respect to his body axis, with the first device for production of the first magnetic treatment field being arranged on the first cantilever arm, and being located at the side of the patient, away from the rest plane, in an operating position. This results in a relatively small and localized treatment area.

Nowadays, it is admittedly assumed that magnetic field treatments such as these have no side effects, or virtually no side effects, but it is nevertheless advantageous to define the treatment area relatively accurately. This represents one of the considerable advantages of the invention. Since the device for production of the first magnetic field can be moved virtually directly to the body surface of the patient—possibly separated only by a textile casing—specific body areas can be treated deliberately. The treatment area and the load on the patient (even if it is only a potential load) are thus reduced to a minimum.

The proximity to the patient even results in a multiplication effect. Since it is possible to use smaller coil systems than in the case of known apparatuses, the field curvature is greater, that is to say, overall, the magnetic field has a smaller physical extent, thus further improving the localization of the treatment.

The apparatus is preferably in the form of a treatment stool or seat, with the rest being formed by the backrest of the stool or seat, and the cantilever arm being arranged in the area of the patient's head. The use of an adjustable reclining seat, similar to a television comfort seat, has been found to be particularly comfortable for the patient. A treatment apparatus such as this is particularly highly suitable for carrying out treatments in the head area of the patient.

This embodiment has the advantage that the apparatus can be used even in relatively small doctor's practices. However, for example, use in relatively large treatment centers is also within the scope of the invention, when the rest is a section of a treatment couch.

However, the psychologically advantageous effect of a stool or seat on the patient in comparison to a couch should not be underestimated.

Within the scope of the invention, it has been found that treatment in the case of tinnitus patients can result in a noticeable improvement in the symptoms. This is even more surprising because of the fact that little is yet known about the cause of tinnitus and, so far, the main emphasis has been on trials with treatment medication. The apparatus according to the invention has for the first time allowed the head and cervical spine area to be treated, in which case the areas in which the magnetic field treatment is effective may even be restricted—without any restriction to generality—to partial areas of the head, for example the inner ear. This is because it has been found that spinal column damage or blood circulation illnesses may frequently have a cause which can be positively influenced by the apparatus according to the invention.

The selective treatment of specific subareas of the brain has, in addition to this, also led to positive results following strokes.

Further treatment successes can be achieved in the field of jaw arthrosis, parodontitis (jaw weaknesses) and in the case of degenerative jawbone changes, whose treatment has in the past likewise been focused on traditional therapies, in this case invasive therapies. Furthermore, it has been found that the ingrowth of jaw implants can be assisted.

Initial results even lead to the conclusion that there is increased collagen formation in the treatment area, so that the apparatus according to the invention can be used, inter alia, for cosmetic treatment and for skin conditions.

The cantilever arm preferably has a contact section which is at a distance from the rest and on which the first device for production of the first magnetic treatment field is arranged, with the contact section being suspended such that it can move, in order to allow it to be moved with the first device and to be applied to the body region of the patient to be treated.

According to one advantageously simple refinement of the invention, the cantilever arm has one or more joints, by means of which the cantilever arm is suspended on the apparatus such that it can pivot, in particular on a plane transversely with respect to the rest plane or transversely, in order to produce the movement of the first device for production of the first treatment field, and to apply the contact section to the body.

If a plurality of joints are used, these are connected to form a joint chain, thus resulting in high flexibility so that the contact section can be aligned such that it is individually matched to the body shape of the patient, in order to apply this to the patient, for example, over as large an area as possible and at the desired point. In order to provide robustness for the joint chain, it has been found to be advantageous for a strengthening strip to be interwoven in the joint chain. It is also possible to mechanically prestress the cantilever arm towards the patient.

According to one advantageous development of the invention, the cantilever arm has an outer textile casing, which preferably allows close contact and encases the first device for production of the first magnetic treatment field, a holding frame on which the first device is mounted, and/or the joints. In consequence, these elements are protected and the apparatus has a pleasant appearance and is convenient.

The cantilever arm preferably has an essentially flat cross section, for example being at least twice as high as it is wide, and in particular the pivoting making it possible to apply its flat face to the body region of the patient to be treated. The cantilever arm preferably has a cross section of 1 cm to 20 cm by 2 cm to 40 cm, in particular 2 cm to 10 cm by 5 cm to 25 cm.

According to one particular embodiment, the apparatus has at least one second cantilever arm, which is identical to the first cantilever arm but with mirror-image symmetry with respect to the first cantilever arm in relation to the patient, that is to say with the second cantilever arm also projecting out of the rest plane, and with a second device for production of a second magnetic treatment field, which is designed in the same way as the first device, being arranged on the second cantilever arm, in such a way that a body area of the patient, in particular the patient's head, is positioned between the first and the second device once the patient is seated or is in the treatment position. In consequence, the two contact sections can be moved towards one another and away from one another.

It is particularly preferable for the apparatus to also have a third device for production of a third magnetic treatment field in a third treatment area, with the third device being arranged in particular on the rest and parallel to it, so that the first, second and third devices form a U-shaped arrangement.

The first and second devices are thus advantageously arranged at the side of the patient's head, and the third device is arranged at the rear of the head or on the patient's spinal column, once the patient is seated on the apparatus and the apparatus is in the operating position.

This arrangement has made it possible to achieve a considerable improvement in the symptoms, particularly for the treatment of tinnitus. Without any claim that this is the correct answer, this could be a result of both inner ear areas of the patient and specific areas of the head and/or of the spinal column being subjected to treatment at the same time.

Furthermore, a movement device can be provided, on which the first and second cantilever arms are suspended, in order to move the first and second devices along the apparatus or body axis of the patient or transversely with respect to the cantilever arms, so that it is possible to treat different body areas of the patient.

The movement device is preferably composed of at least one rail and a carriage which can be moved translationally along the rest on this rail, to be precise essentially vertically when the rest is in an upright position, with the rail preferably being attached to the rear piece of the rest.

The first and second cantilever arms are also attached to the carriage, so that the first and second devices can be moved along the body axis (axis of symmetry) of the patient.

A locking device is preferably also provided, in order to lock the movement of the carriage on the rail.

Furthermore, the first and second cantilever arms are preferably detachably attached to the movement device, so that the elongated cantilever arms can be replaced, for example in order to treat other body areas or in order to make it possible to match the apparatus to the body structure of the patient.

According to one particularly preferred embodiment, the first, second and/or third devices or device for production of the magnetic field each form or forms an arrangement for production of nuclear magnetic resonance, with a basic coil producing a basic magnetic field during operation, in which the nuclei to be excited precess, and a resonant alternating electromagnetic field is injected by means of two RF coils in each case.

The magnetic field treatment is thus carried out in particular by the production of nuclear magnetic resonances (NMR). The nuclear magnetic resonance condition in accordance with the equation $\omega=\gamma \times B0$, where $\omega$ is the circular frequency of the alternating RF field, $\gamma$ is the gyromagnetic ratio of the atom nuclei to be excited, and $B0$ is the magnetic induction of the basic field, does not need to be explained in any more detail to a person skilled in the art.

However, other treatment methods are also possible, for example, by means of constant or alternating magnetic fields.

In order to produce NMR, the devices for production of the magnetic treatment fields are preferably in the form of coil arrangements and each have at least one first and second magnetic field generator, in particular in the form of a first and second coil system, respectively. The treatment fields are also each formed by superimposition of the magnetic fields of the respective first and second magnetic field generators, with these two magnetic fields in each case being superimposed essentially at right angles in the associated treatment area.

The coils of the respective first and second coil systems are preferably arranged parallel and/or on the same plane, so that the first, second and/or third devices or device each have or has essentially flat cross sections, thus making it possible to achieve a flat design. The plane or coil plane of the first and second devices extends transversely with respect to the rest plane and/or transversely with respect to the body axis of the patient in the operating position, so that side areas of the patient can be treated specifically when the contact sections are applied at the side, for example on the head, of the patient. The coil plane of the third device in contrast runs essentially parallel to the rest plane.

The first coil systems each have or comprise a basic coil, and the second coil systems each have or comprise two RF coils, in particular for production of the resonant alternating electromagnetic field for the NMR.

Furthermore, the two RF coils are each arranged alongside one another, preferably within the opening in the flat basic coil, and are connected in opposite senses such that, despite the parallel arrangement, the magnetic fields of the first and second coil systems are superimposed centrally and at right angles by means of the respective device. The respective treatment or NMR area is located at a distance of about 1 cm to 30 cm, preferably about 2 cm to 10 cm, and particularly preferably about 3 cm±1 cm from the upper face of the coils. These dimensions have been found to be particularly advantageous for the symptoms to be treated.

The magnetic induction of the basic magnetic field of the NMR is preferably between 0.1 Gauss and 1000 Gauss, in particular between 1 Gauss and 100 Gauss. The frequency f of the RF field for hydrogen accordingly corresponds to 422.5 Hz to 4.225 MHz, preferably 4.225 kHz to 422.5 kHz, according to the equation $$f[\text{kHz}]=4.225 \times B0[\text{Gauss}].$$

The nuclear magnetic resonance is particularly preferably produced periodically, with the repetition frequency of the period nuclear magnetic resonance excitation, preferably being 1 Hz to 1000 Hz, in particular 5 Hz to 100 Hz, and particularly preferably up to 40 Hz, in particular with the RF field being injected discontinuously with this period, for example within a square-wave envelope.

The invention will be explained in more detail in the following text using exemplary embodiments and with reference to the drawings, in which identical and similar elements are in some cases provided with the same reference symbols, and features of different exemplary embodiments can be combined with one another.

DETAILED DESCRIPTION OF THE INVENTION

Figure 1:
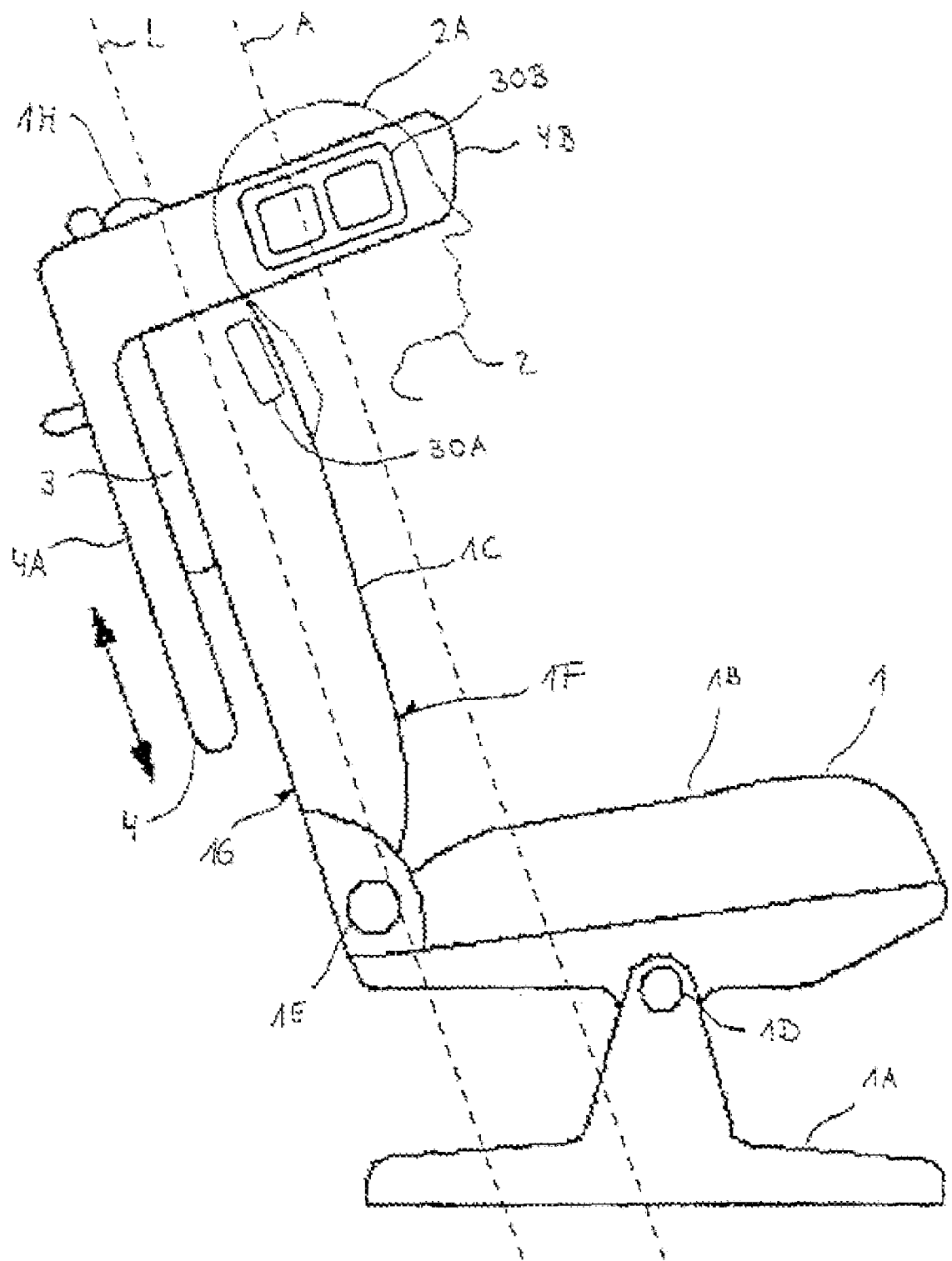
FIG. 1 shows a schematic side view of a treatment seat according to the invention.

With reference to FIG. 1, the apparatus according to the invention for therapeutic treatment with magnetic fields is illustrated in the form of a treatment seat 1. The treatment seat 1 has a foot 1A, a seat surface 1B and a rest or backrest 1C, which defines a rest plane L running essentially parallel to the body axis A. The treatment seat 1 is designed in a similar manner to a relaxing chair, in such a manner that the seat surface 1B can be inclined about a joint 1D, and the backrest 1C can be inclined about a joint 1E in order to provide a comfortable treatment position for the patient.

For treatment, the patient 2 (of whom only the head 2A is illustrated for the sake of clarity) sits on the treatment seat 1 and rests his back on the front face 1F of the backrest 1C.

A movement device 3 is attached to a rear face 1G (which is opposite the front face 1F) of the backrest 1C, and a holding frame 4 is suspended on this movement device 3 such that it can be moved along the backrest 1C or parallel to the body axis A of the patient 2.

The holding frame has a holding section 4A and two mirror-image symmetrical cantilever arms 4B, 4C, of which only the right-hand cantilever arm 4B can be seen in FIG. 1, and with the holding section 4A and the cantilever arms 4B, 4C essentially forming an L-shape or a right angle when viewed from the side. The essentially narrow side cantilever arms 4B, 4C extend like blinkers from back to front or transversely with respect to the body axis A long the patient's head 2A.

A device 30B, 30C for production of the treatment field, and in the form of a respective coil arrangement 30B, 30C is respectively attached to the side cantilever arms 4B, 4C. For this purpose, the moving cantilever arms 4B, 4C are, for example, in the form of holding frames composed of non-magnetic material, and the coil arrangements 30B, 30C are mounted within the respective frame.

A third coil arrangement 30C is arranged within the backrest 1C, for example in the area of the back of the head or cervical spine area of the patient 2.

Alternatively, the third coil arrangement 30A can also be fitted outside the backrest 1C, on its front face 1F, and can be suspended by means of a holding strip, which runs over the upper face 1H of the backrest 1C and the holding section 4A. In this case, one end of the holding strip is connected to the third coil arrangement 30A, and the second end of the holding strip is connected to the backrest 1C, so that the third coil arrangement 30A is automatically moved together with the holding frame 4 along the body axis A. This embodiment ensures that the three coil arrangements 30A, 30B, 30C remain at least approximately in the same position with respect to one another during movement of the holding frame 4.

Figure 2:
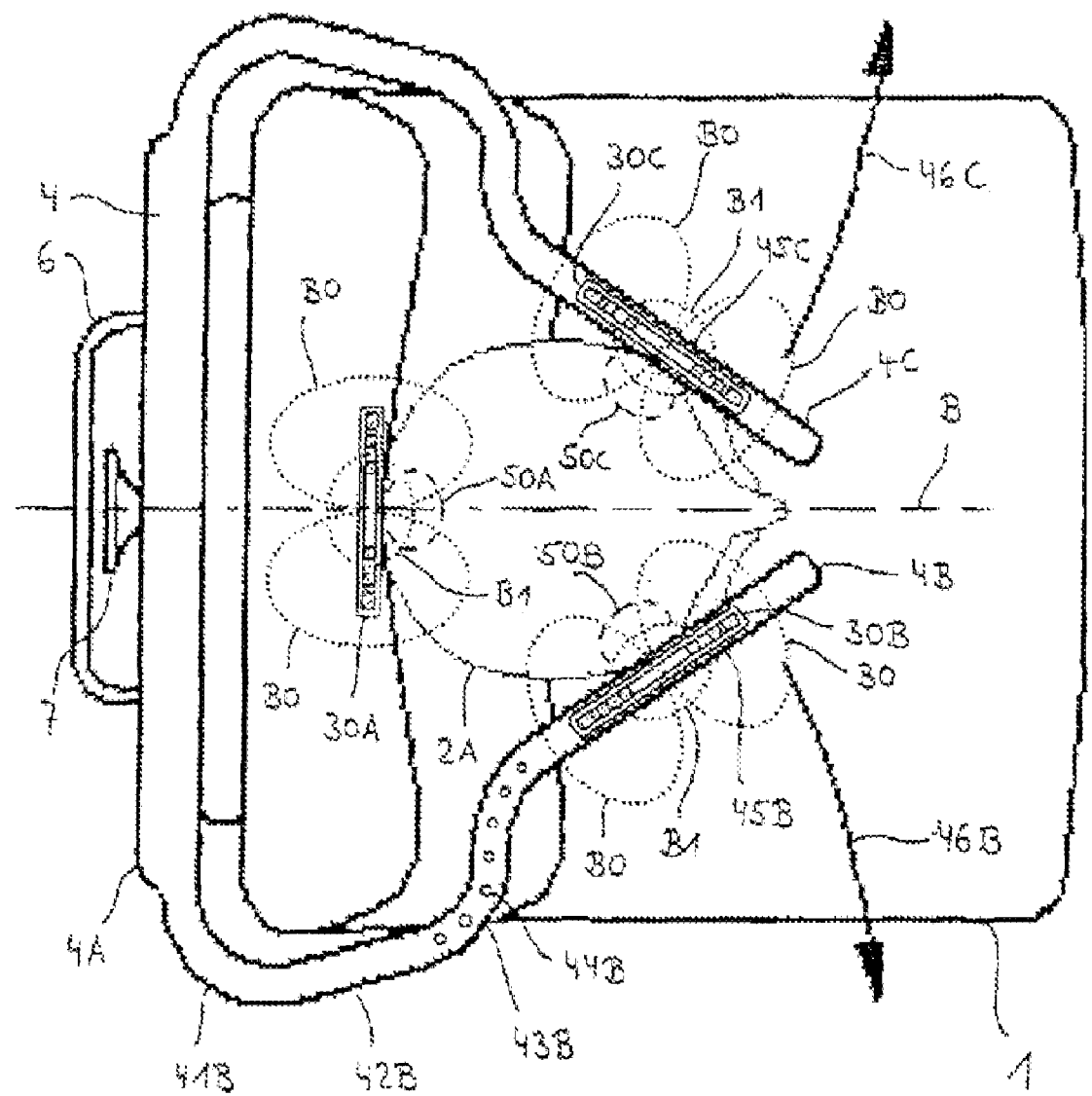
FIG. 2 shows a schematic plan view from above of the treatment seat in FIG. 1.

FIG. 2 illustrates the treatment seat 1 with the patient 2 schematically in the form of a plan view from above, with the illustration likewise showing the coil arrangements 30A, 30B and 30C—although they are concealed in reality.

The right-hand cantilever arm or coil cantilever arm 4B is attached by means of a curved connecting section 41B to the holding section 4A, then extends forwards with a straight section 42B, after which it has a jointed section 43B with a plurality of joints 44B, which form a joint chain in order to allow the jointed section to be shaped in a versatile manner. In the illustrated operating position, the jointed section 43B is essentially S-shaped.

The coil arrangement 30B is attached to an essentially straight contact section 45B which is at a distance from the holding section 4A and is adjacent to the jointed section 44B. The contact section 45B (which is located at the front end of the cantilever arm 4B) as well as the coil arrangement 30B in this example extend obliquely forward and inward from above, in a plan view, in order to treat the left-hand and right-hand areas of the face, and the coil arrangements 30A, 30B and 30C form a U-shape, or run along the sides of a triangle. The coils are thus arranged in such a manner that the magnetic lines of force each emerge from the coils transversely with respect to the rest and transversely with respect to the body axis A.

The joints 44B allow the cantilever arm 4B to be moved away from the patient's head 2A and back toward it again, to be more precise to be pivoted along the arrow 46B in such a manner that the contact section 45B can be moved with the coil arrangement 30B, to be precise can be moved away from the patient and toward the patient. The coil arrangements 30B, 30C can thus be moved at least two-dimensionally by the combination with the movement device 3.

In the operating position, the contact section 45B is located at the body region of the patient 2 to be treated, or is located at least in its immediate proximity. The contact section 45B together with the coil arrangement 30B arranged in it is surrounded by a textile casing, plastic casing or some other cladding materials, although this is not illustrated in the figures.

The overall arrangement is mirror-image symmetrical around the axis of symmetry B of the patient, so that the left-hand cantilever arm 4C and the left-hand coil arrangement 30C are identical, but in mirror-image form.

Each of the three coil arrangements 30A, 30B and 30C produces a basic magnetic field B0 and an RF field B1, which are superimposed essentially at right angles to the respective treatment area, in the respective treatment area 50A, 50B, 50C, with at least parts of these treatment areas being located in the interior of the patient's body. In this case, the treatment areas 50A, 50B, 50C each face one another on the inside and face the patient. In other words, the body region of the patient to be treated is located within the respective treatment area.

The three treatment areas cannot, of course, be delineated exactly and are thus illustrated only schematically by means of dashed lines with the reference symbols 50A, 50B and 50C.

The size and position of the respective treatment areas 50A, 50B and 50C may vary within certain limits as a result of the tuning of the magnetic fields. The three treatment areas 50A, 50B, 50C may, of course, also overlap to form a common treatment area.

Figure 3:
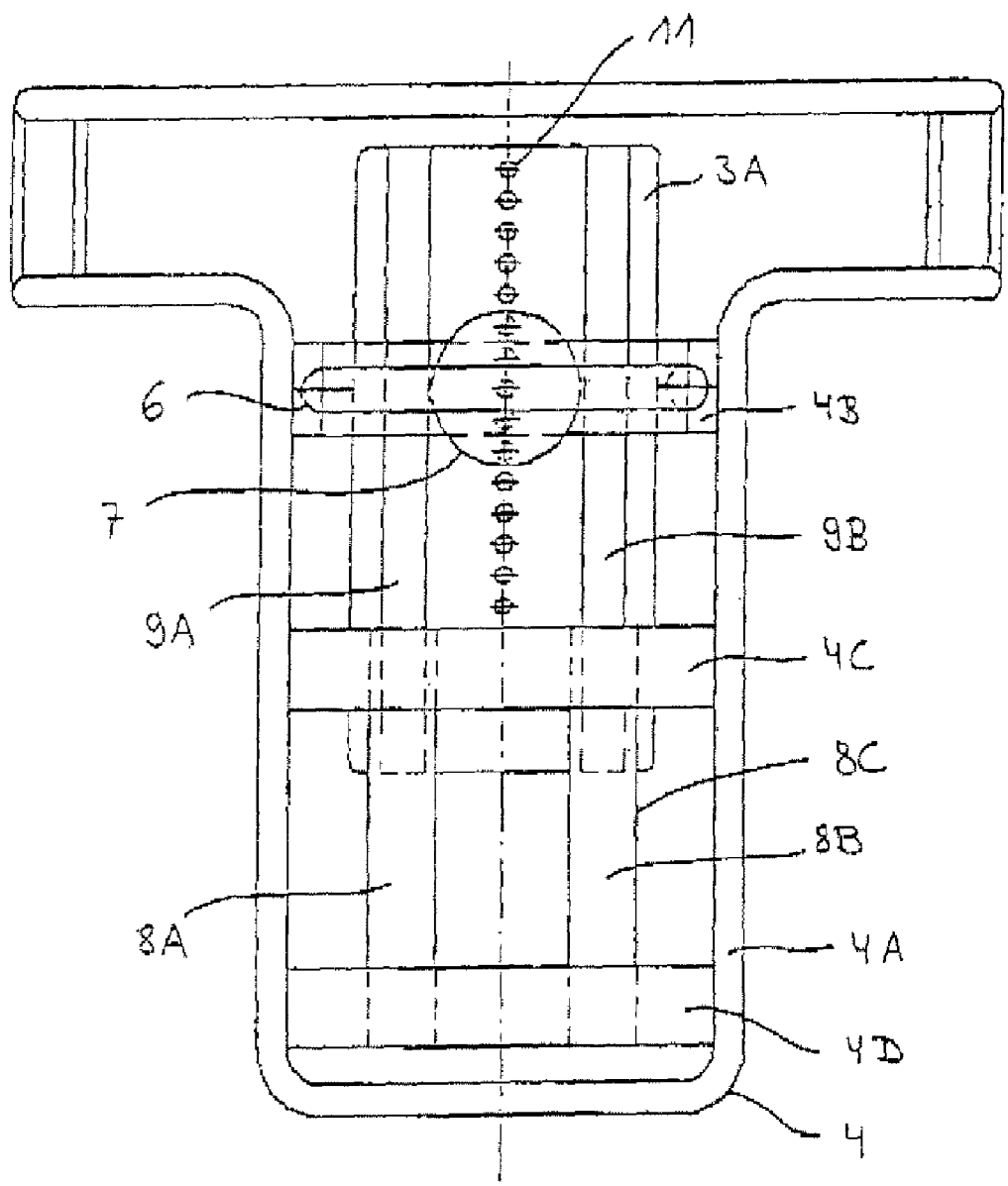
FIG. 3 shows a schematic rear view of a movement device on the treatment seat.

FIG. 3 shows a rear view of the holding frame 4.

The holding frame 4 has the holding section 4A, an upper, middle and lower transverse strut 4B, 4C, 4D and two movement rails 8A, 8B, which form a movement carriage 8C. The movement carriage 8C slides on a rail in the form of an adaptor plate 3A, which is attached to the rear face 1G of the backrest 1C.

The adaptor plate 3A has a plurality of vertically arranged holes 11, in which a latching pin, which is fitted on a pull-button 7, latches as a locking means in the respectively desired position, in order to lock the movement of the holding frame 4. The pull-button 7 is in this case arranged in the area of the movement handle 6, in order to ensure easy handling.

For servicing and repair purposes or for other medical indications, the holding frame 4 can be removed together with the cantilever arms 3B and 3C from the seat 1, and can be replaced. This is done by releasing a lock and by pulling the movement carriage 8C upward along the rails. An adjusting handle 6 for manual movement of the holding frame 4 is also permanently fitted to the holding section 4A.

Figure 4:
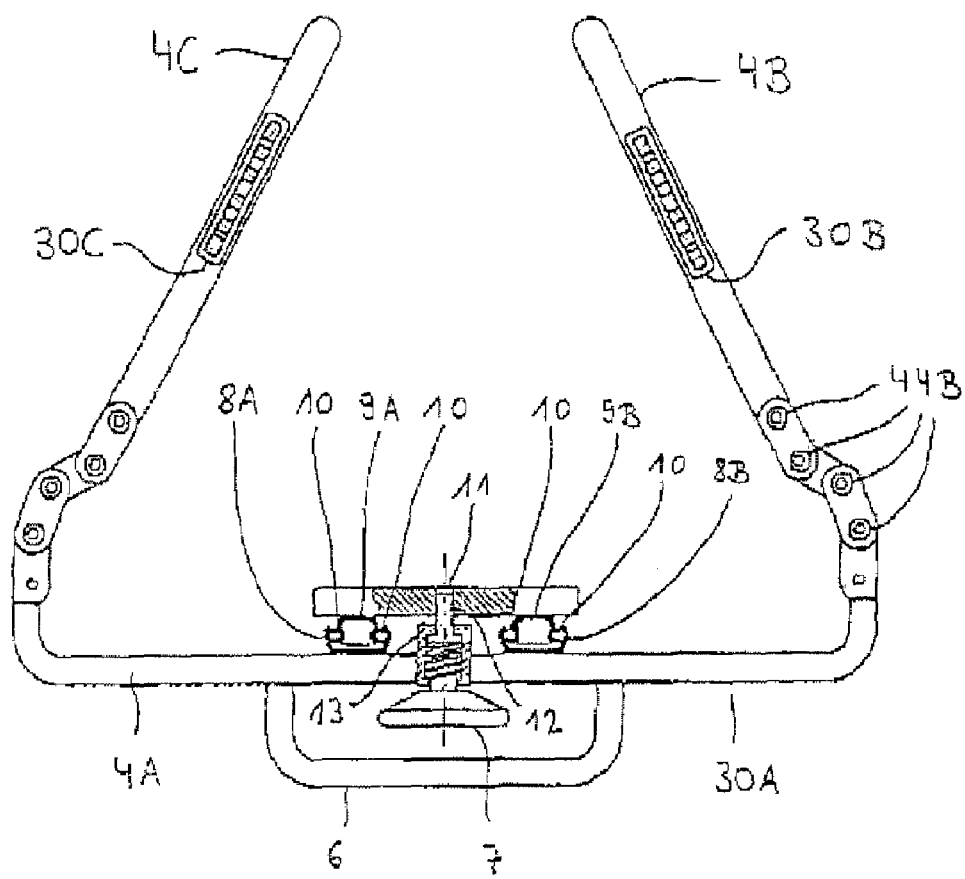
FIG. 4 shows a schematic plan view from above of the movement device shown in FIG. 3 with cantilever arms.

FIG. 4 shows a cutaway plan view from above of the movement mechanism and the cantilever arms without the textile sheath.

In particular, the illustration shows how the movement rails 8A, 8B can be moved on the movement rails 9A, 9B of the adaptor plate, with balls 10 forming a ball bearing. This also illustrates how the latching pin 12 engages in the hole 11 in the hole pattern.

The figure also shows the capability to move the cantilever arms 30B, 30C transversely in a flexible manner by means of the joint 44B and link elements 14, 15 located between them, which together form the joint chain of each cantilever arm.

The cantilever arms 30B, 30C are detachably attached to the common holding section 4A by attachment means which are not illustrated.

Figure 5:
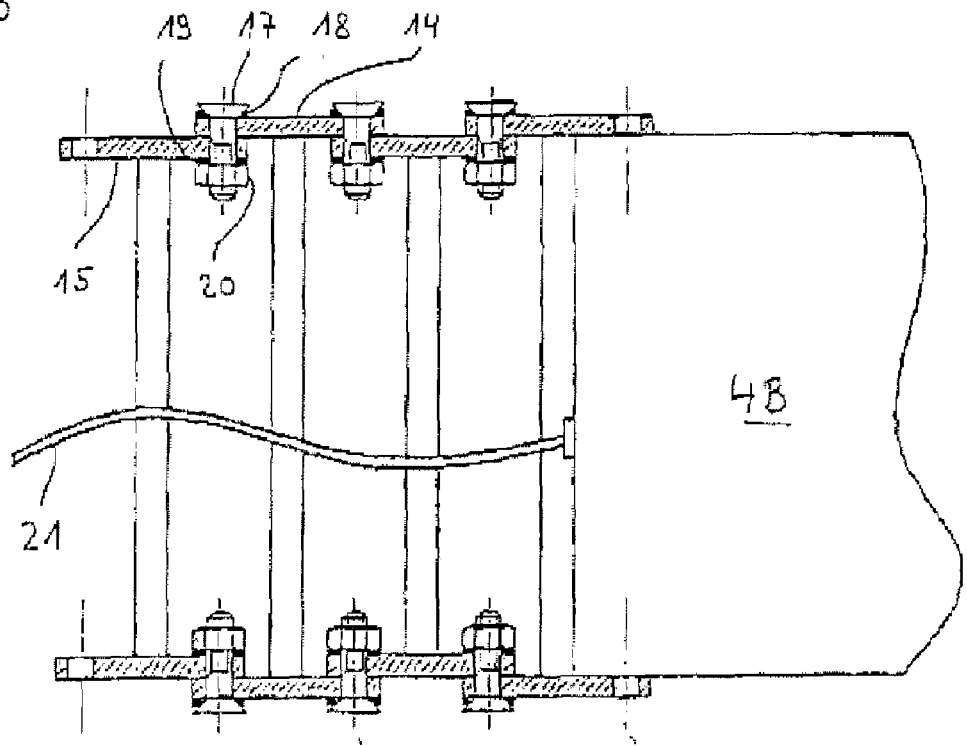
FIG. 5 shows a side view, in the form of a detail, of a cantilever arm with a joint chain.

FIG. 5 shows a side view of the link elements 14, 15, which are connected to one another in pairs by means of compression elements 17, compression rings 18, washers 19 and nuts 20, in a slightly clamped manner such that they can rotate. The figure also shows an electrical supply line 21 for the coil arrangements.

Figure 6:
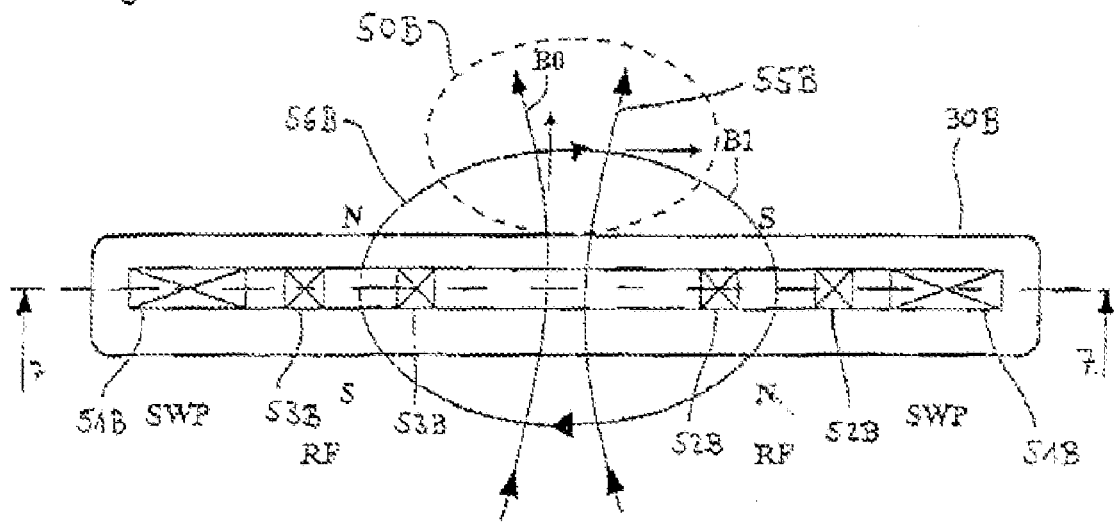
FIG. 6 shows a schematic cross section along the line 6-6 in FIG. 7 through a device according to the invention for production of a treatment field.

FIG. 6 shows the coil arrangement 30B, representing all three identical coil arrangements 30A, 30B, 30C schematically in the form of a cross section parallel to the coil plane.

The coil arrangement 30B has a basic coil 51B for production of the virtually constant basic field B0, whose magnetic lines of force 55B emerge centrally at right angles from the coil arrangement 30B, as well as two RF coils 52B, 53B.

The two RF coils 52B, 53B are polarized in opposite senses, so that the magnetic lines of force 56B of the alternating magnetic field B1 emerge upward on the upper face of the left-hand RF coil 53B, and enter the coil arrangement again on the upper face of the right-hand RF coil 52B. In the treatment area 50B, this results in the magnetic fields B0 and B1 produced by means of coils 51B, 52B, 53B (which are arranged parallel) being essentially at right angles to one another despite the fact that they emerge from the coils parallel, thus making it possible to satisfy the nuclear magnetic resonance conditions in the treatment area 50B.

Figure 7:
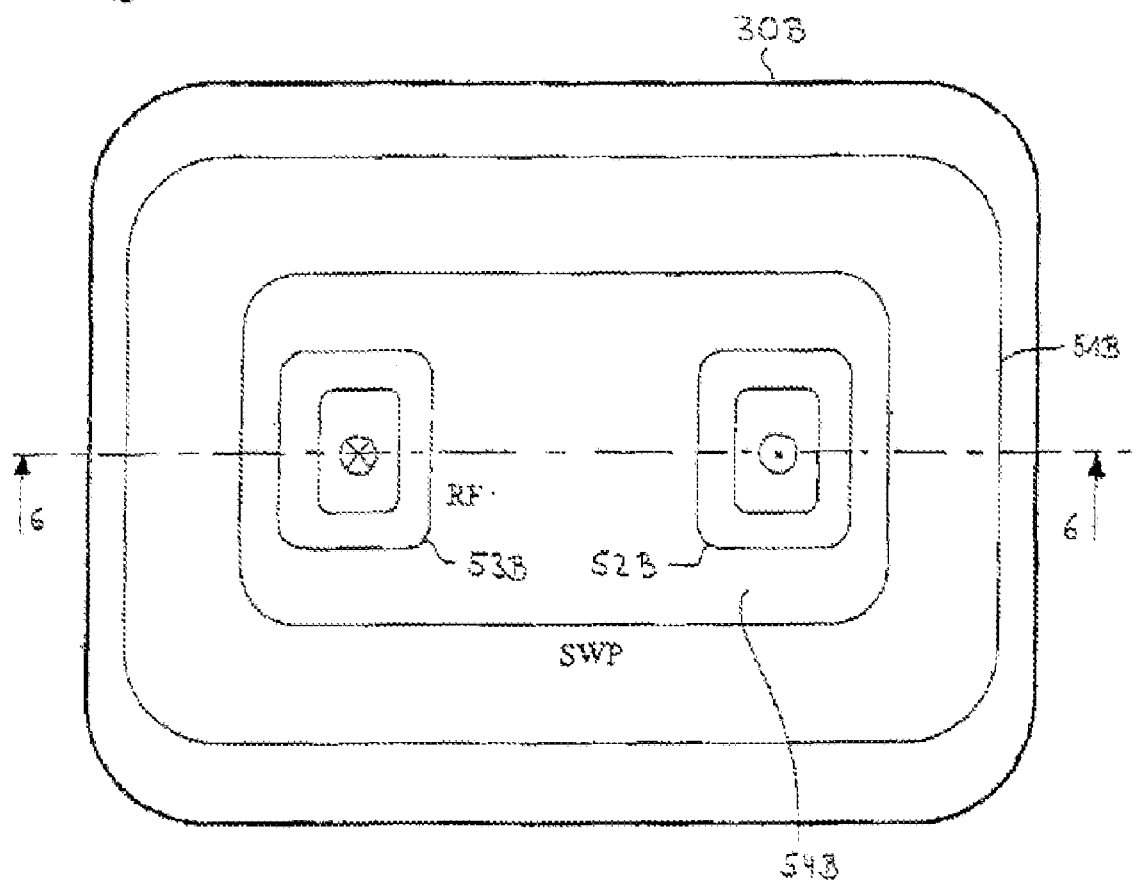
FIG. 7 shows a schematic cross section through the device shown in FIG. 6 along the line 7-7.

FIG. 7 shows a section illustration along the line 7-7 in FIG. 6, with the line 7-7 representing the coil plane. 6-6 shows the section line for the illustration in FIG. 6.

As can be seen from FIG. 7, the two RF coils 52B, 53B are arranged within the opening 54B to the basic coil 51B.

The planar arrangement of the basic coils 51B and of the RF coils 52B and 53B according to the invention makes it possible to generate orthogonal magnetic fields in the treatment area. In this case, in the treatment area, the basic or sweep coil 51B produces the virtually constant magnetic field B0, which is vertical with respect to the coil plane, and the two radio-frequency coils 52B, 53B within the sweep coil produce the alternating magnetic field B1, which is parallel to the coil plane, in the treatment area.

The shape of the coil arrangement can also be matched appropriately to the application and the body shape, for example it can be curved for joint damage. An embodiment of the invention such as this (not illustrated) has been proven in particular for the treatment of animals. For example, the coil arrangement can be attached to a gaiter, in particular by being stapled to it, which can be used, for example, for the treatment of horse fetlocks.

A soft treatment cover has also been successfully used, which is placed over the back of a horse and to which one or more coil arrangements can be detachably attached, for example by means of a Velcro strip, at any desired point.

The RF coils 52B, 53B furthermore have a series inductance L and, together with a capacitor C, form a tuned circuit. The electrical natural resonant frequency F is given by:

$$F = \frac{1}{2\pi\sqrt{LC}}$$

In this case, the natural resonant frequency and the nuclear magnetic resonance frequency are matched to one another so that the RF transmitter in the controller automatically generates an AC voltage at the frequency F, in order to produce alternating fields that are as large as possible, with a relatively small amount of energy.

Each of the coil arrangements 30A, 30B, 30C produces the two orthogonal magnetic fields B0 and B1 which are in each case required for the nuclear magnetic resonance process, in accordance with the equation which is applicable to protons, which make up about 80% of the atom nuclei which occur in human and animal bodies:

$f$ [kHz]=4.225×$B0$ [Gauss]

The magnetic treatment area B0 is in this case composed of a constant or static component B01 and a smaller modulation component B02, that is to say B0 is virtually constant. The frequency f is in this case tuned to the constant component B01.

By way of example, B01=4 Gauss, and the frequency f=16.9 kHz.

The magnitude of the variable magnetic field component B02 is about 10% to 100%, preferably 20% to 70%, and most preferably about 50%±10% of the magnitude of B01. The variation of the modulation component B02 compensates for the inhomogeneity of B01. In other words, the basic magnetic field B0 is modulated in such a manner that the nuclear magnetic resonance condition is satisfied, at least at times, over the entire treatment area. In other words, the natural inhomogeneity of B0 in conjunction with the modulation by means of B02 is used in order to scan the resonance condition over the treatment area.

Figure 8:
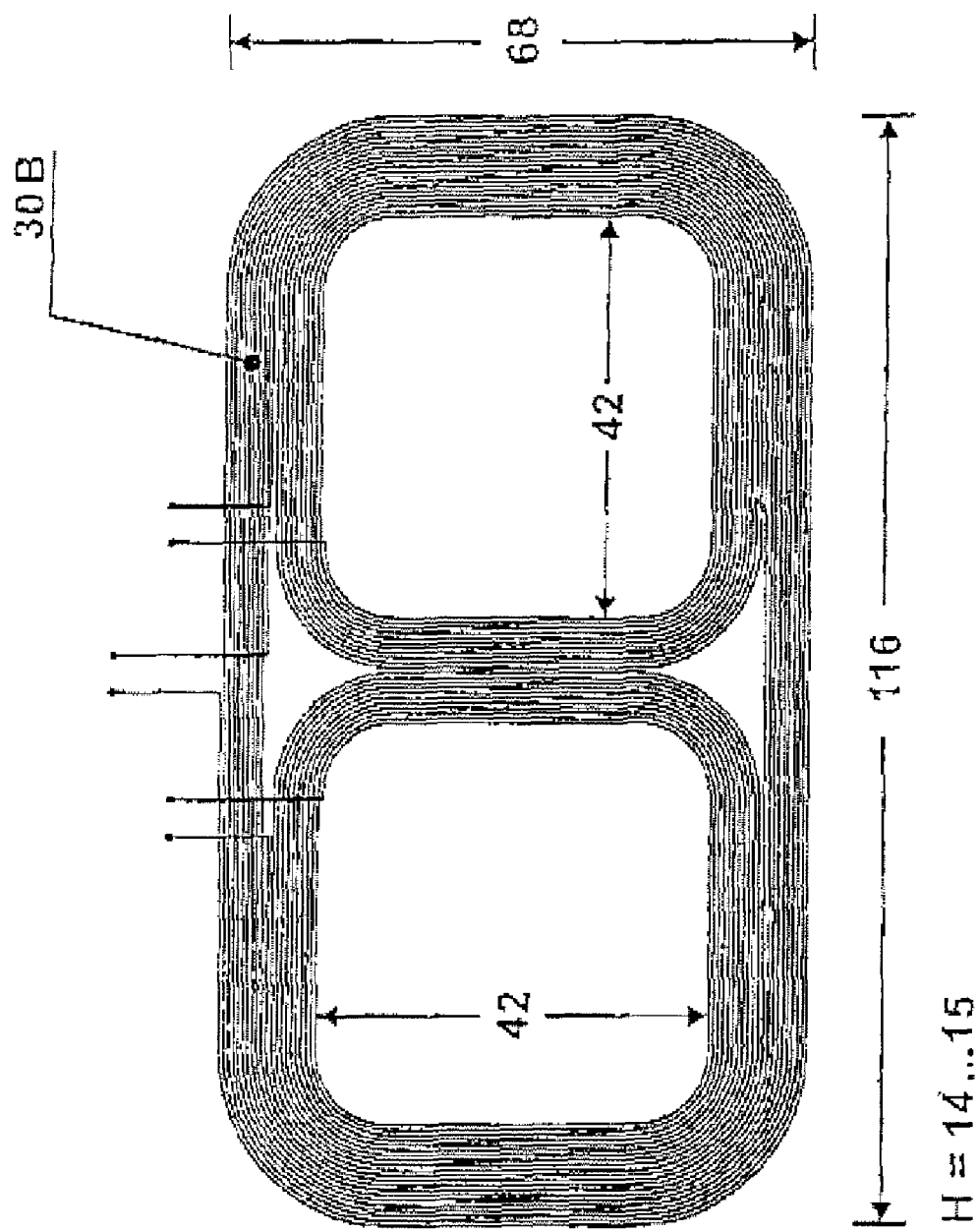
FIG. 8 shows a photograph of the device shown in FIG. 7.

FIG. 8 shows a photograph of the coil arrangement 30B with dimensions. The coil arrangement has a length of L=116 mm, a width B=68 mm and a height H=15 mm. The opening in each of the essentially square RF coils 52B, 53B is about 42 mm square. However, a variation of the size to a range from about one twentieth, one fifth, one third or one half up to about twice, three times, five times or twenty times a stated dimension is also within the scope of the invention.

Figure 9:
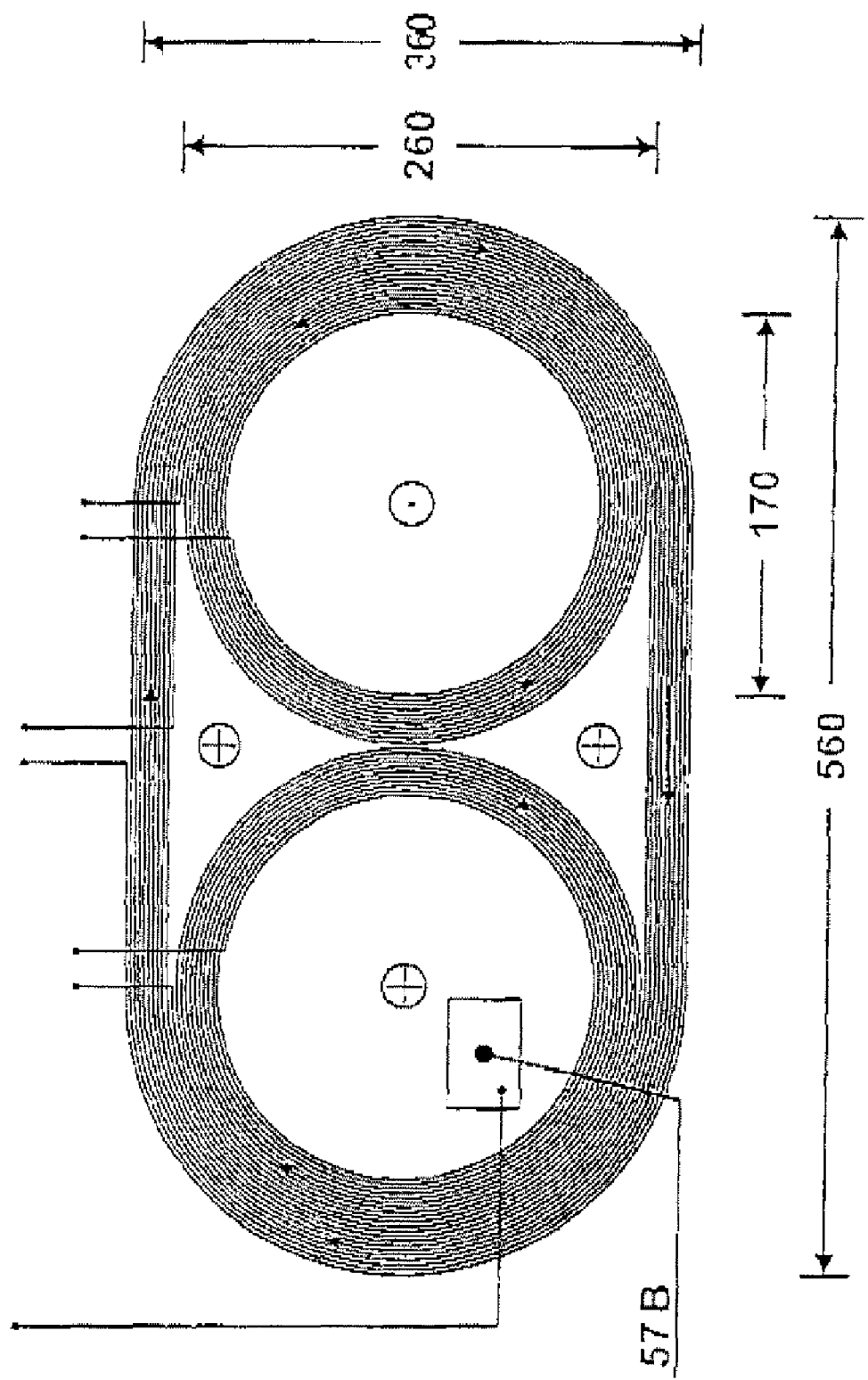
FIG. 9 shows a photograph of a device for production of the treatment field according to a further embodiment of the invention.

FIG. 9 shows an alternative embodiment of the coil system with essentially circular RF coils and an oval basic coil around the RF coils. Furthermore, a tuning element 57B is provided, and is fitted within the coil arrangement. The tuning element 57B is used to detect the NMR signal and to match the basic field B0 and/or the RF field B1, so as to form a control loop for controlling the magnetic fields for nuclear magnetic resonance.

Figure 10:
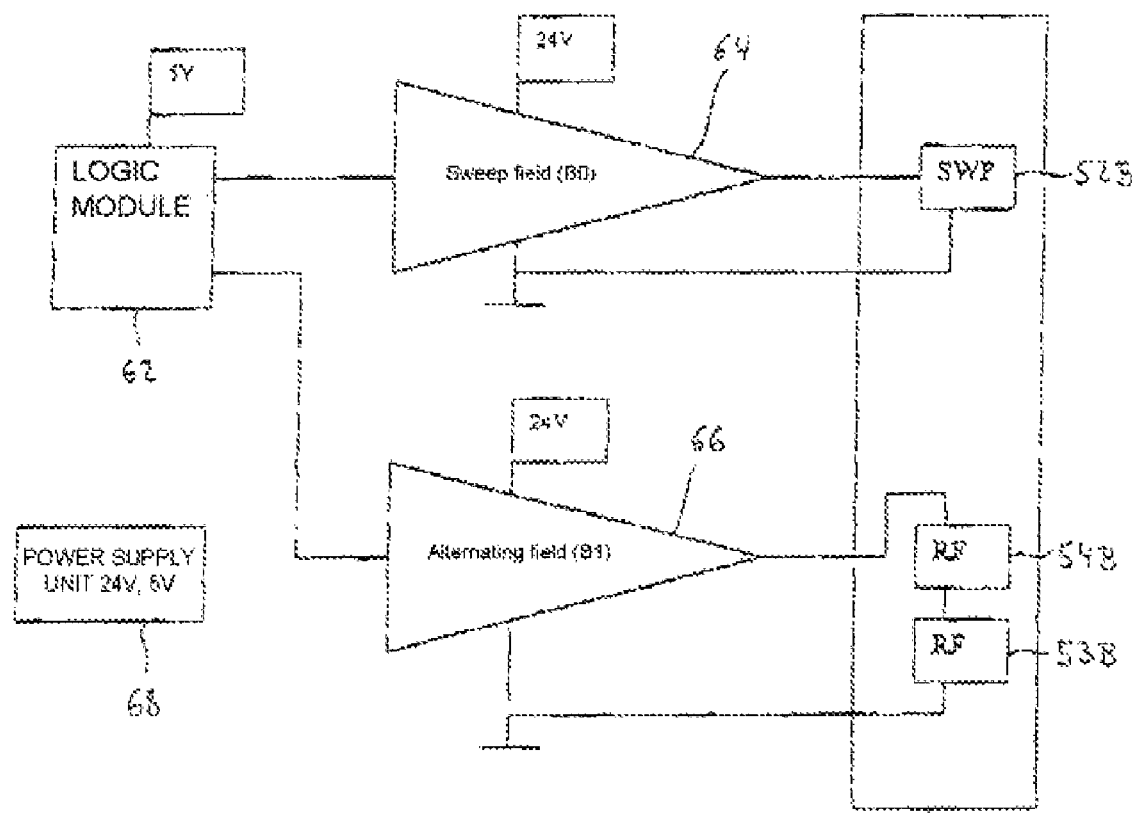
FIG. 10 shows a block diagram of a controller.

FIG. 10 shows a block diagram of the control electronics. A logic module 62 controls a drive device 64 for the basic or sweep coil 51B, and a drive device 66 controls the two RF coils 52B, 53B, which are connected in series. Furthermore, the apparatus is supplied with electrical power from a power supply unit 68. The controller can in this case drive one, two, three or more coil arrangements.

Figure 11:
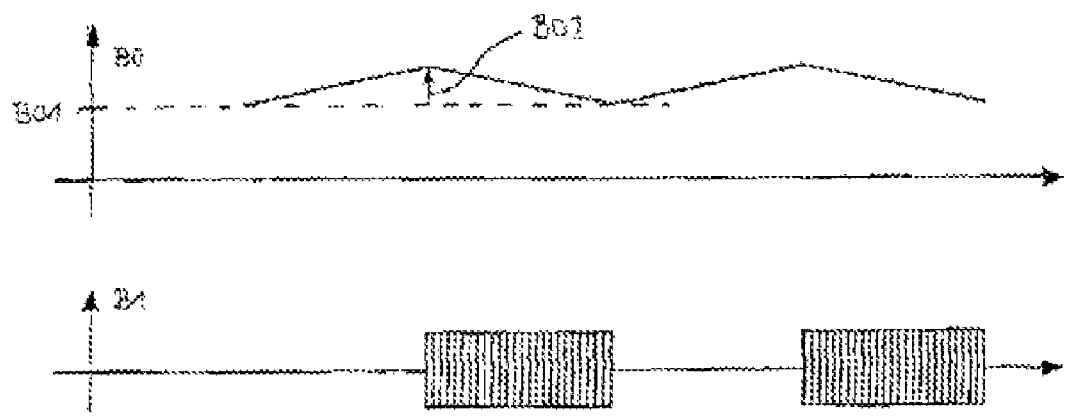
FIG. 11 illustrates an example of the time profile of the intensity of the magnetic fields.
Figure 12:
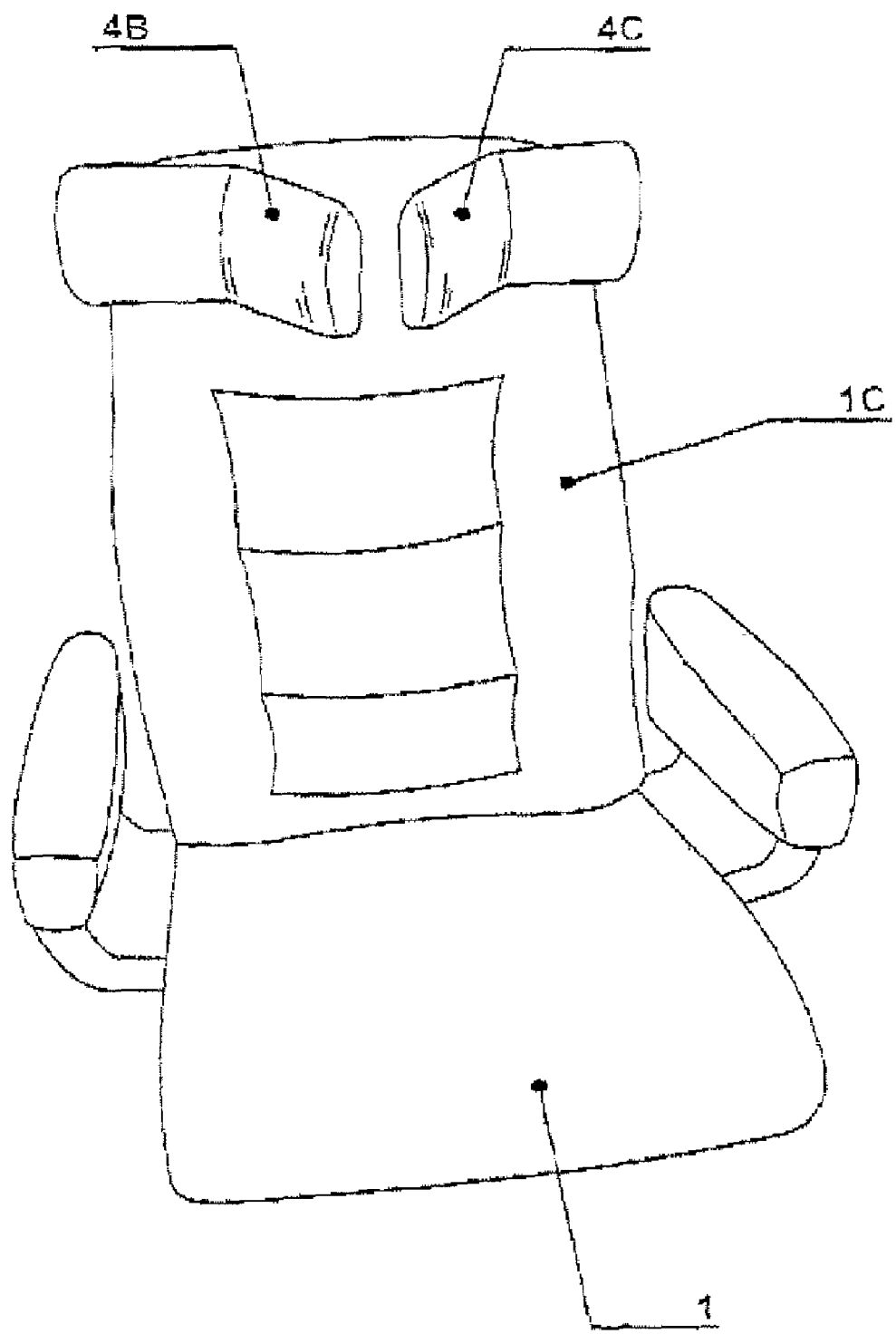
FIG. 12 shows a photograph of one embodiment of the treatment seat according to the invention.

FIG. 11 shows an example of a magnetic field profile for periodic nuclear magnetic resonance production. The basic field B0 has a constant basic level B01 and a component B02 which varies with time, in this example corresponding to triangular-waveform modulation. The alternating field B1 is injected discontinuously and periodically with a square-wave envelope during the falling flanks of the basic field B0. In other words, the alternating field B1 is active on the falling flanks B0, and is equal to zero on the rising flanks, which is also referred to as a fast adiabatic passage. The hydrogen nucleus magnetization in the body is in this case tilted through 180° in each case.

Table 1, below, shows particularly advantageous values for treatment.

TABLE 1

| | |
|---|---|
| Alternating field (B1) | 2 kHz to 40 kHz, in particular about 30 kHz |
| B1 amplitude | 0.02 mT to 0.15 mT, in particular about 0.05 mT |
| Virtually-constant magnetic field (B01) | 30 mm above the coil system 0.1 mT to 1.0 mT, in particular about 0.7 mT |
| Magnetic field sweep (B02) | 20% to 50% of B01, in particular about 30% |
| Modulation frequency of B02 | 1 Hz to 250 Hz |
| Modulation type of B02 | Triangular, square-wave, sinusoidal, triangular particularly preferable |

However, frequencies of the alternating field B1 of 5 kHz to 1 MHz have also been proven for larger coil arrangements.

It is obvious to a person skilled in the art that the embodiments described above should be regarded only as examples and the invention is not restricted to them, but can be varied in many ways without departing from the essence of the invention.

What is claimed is:

1. An apparatus for therapeutic treatment of a patient using magnetic fields comprising:
    a first device for production of a first magnetic treatment field within a first treatment area;
    a second device for production of a second magnetic treatment field within a second treatment area;
    a rest for the patient to lie on, in such a manner that a body region of the patient to be treated is positioned in the first treatment area once the patient is in place on the apparatus and the apparatus is in an operating position; and
    a first cantilever arm and a second cantilever arm, the first cantilever arm and the second cantilever arm projecting out of the plane defined by the rest, with the first device being arranged on the first cantilever arm in order to produce the first magnetic treatment field and the second device being arranged on the second cantilever arm, with the apparatus having a movement device on which the first and second cantilever arms are suspended, in order to move the first and second devices essentially along the body axis of the patient, and with the movement device having at least one rail, which is attached to the rear face of the rest, and with the first and second cantilever arms being attached to a carriage which is arranged on the at least one rail such that it can move along the rest.

2. The apparatus of claim 1, with the apparatus being in the form of a treatment seat, and the rest being formed by the backrest of the treatment seat.

3. The apparatus of claim 1, with the first cantilever arm comprising a contact section, which is at a distance from the rest and on which the first device for production of the first magnetic treatment field is arranged, and which contact section is suspended such that it can move, and can make contact with the body region of the patient to be treated.

4. The apparatus of claim 1, with the first cantilever arm being fitted to the apparatus such that it can pivot.

5. The apparatus of claim 1, with the first cantilever arm being designed such that it can pivot on a plane transversely with respect to the rest plane, and making contact with the patient at the side.

6. The apparatus of claim 1, with the first cantilever arm and the second cantilever arm having a plurality of joints which form a joint chain.

7. The apparatus of claim 6, with a stabilization strip being woven through the joint chain.

8. The apparatus of claim 1, with the first cantilever arm having an outer casing, and the first device for production of the first magnetic treatment field, and the joints being arranged within the casing.

9. The apparatus of claim 1, with the first cantilever arm having an essentially flat cross section and being able to make contact with the body region of the patient to be treated with its flat face by means of the pivoting process.

10. The apparatus of claim 1, with the apparatus having a third device for production of a third magnetic treatment field in a third treatment area, with the third device being arranged on the rest, and with the first, second and third devices being arranged essentially in a U-shape.

11. The apparatus of claim 1, with the first and second devices being arranged at the side of the head of the patient and the third device being arranged in the area of the back of the head or the spinal column of the patient, when the patient is in position on the apparatus and the apparatus is in the operating position.

12. The apparatus of claim 1, having a locking device in order to lock the movement of the carriage.

13. The apparatus of claim 1, with the first and second cantilever arms being detachably attached to the movement device in order to replace the first and second cantilever arms.

14. The apparatus of claim 1, with the first device for production of the first magnetic treatment field having a first magnetic field generator and a second magnetic field generator, with the first and second magnetic field generators respectively being in the form of a first and second coil system.

15. The apparatus of claim 14, with the first magnetic treatment field being formed by a superimposition of the magnetic field of the first and second magnetic field generators and with these two magnetic fields being superimposed essentially at right angles in the first treatment area.

16. The apparatus of claim 14, with the first device for production of the first magnetic treatment field having an essentially flat cross section, and the coils of the first and second coil system being arranged on the same plane as that which forms the coil plane, with the coil plane being arranged transversely with respect to the rest plane.

17. The apparatus of claim 14, with the first coil system having a basic coil and the second coil system having two RF coils.

18. The apparatus of claim 17, with the two RF coils being arranged alongside one another and being connected in opposite senses.

19. The apparatus of claim 17, with the two RF coils being arranged parallel within the coil opening of the basic coil.

20. The apparatus of claim 17, with the two RF coils producing an alternating magnetic field during operation.

21. The apparatus of claim 17, with the first device for production of the first magnetic treatment field forming an arrangement for production of nuclear magnetic resonance, with the basic coil producing a basic magnetic field during operation, in which the nuclei to be excited in precession, and a resonant alternating electromagnetic field is injected by means of the RF coils.

22. The apparatus of claim 1, with the magnetic induction of the basic magnetic field being between 0.1 Gauss and 1000 Gauss.

23. The apparatus of claim 1, having means for periodic production of nuclear magnetic resonances.

24. The apparatus of claim 23, with the repetition frequency of the excitation of the nuclear magnetic resonances being in the range of 1 Hz to 1000 Hz.

25. A method for therapeutic treatment of jaw arthrosis, parodontitis, degenerative jawbone changes or to assist the ingrowth of implants of a living body, the method comprising treating the living body by using the apparatus of claim 1.

26. A method for therapeutic treatment of tinnitus of a living body, the method comprising treating the living body by using the apparatus of claim 1.

27. The method of claim 25, with collagen formation in the living body being achieved by means of magnetic fields producible by using the apparatus of claim 1.

* * * * *